Dec. 17, 1974 G. M. RUPPEL Plant Pat. 3,661
GLADIOLUS
Filed Nov. 16, 1972
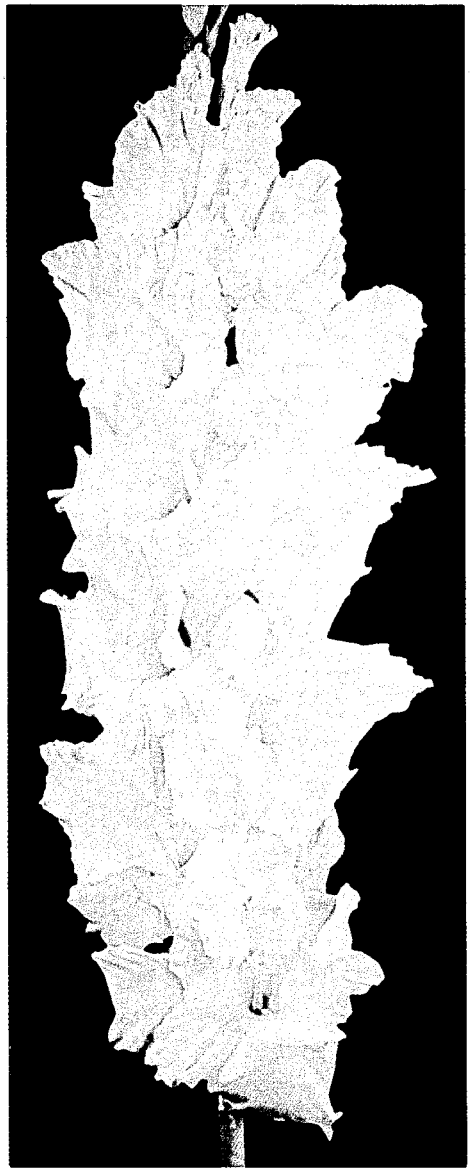

United States Patent Office

Plant Pat. 3,661
Patented Dec. 17, 1974

3,661

GLADIOLUS

George M. Ruppel, Bridgehampton, N.Y., assignor to Selected Glads, Inc., New Albany, Ind.

Filed Nov. 16, 1972, Ser. No. 307,010
Int. Cl. A01h *5/00*
U.S. Cl. Plt.—85 1 Claim

This invention relates to a new and distinct variety of gladiolus plant.

This new gladiolus plant was originated by me by crossing the variety known as "Party Ruffles" (unpatented) with the variety known as "Landmark" (patented as 1,933), "Party Ruffles" being the seed parent, "Landmark" being the pollen parent, both being registered with the North America Gladiolus Registry, published in Sandina, N.Y.

The improved variety resulting from this breeding is evidenced by the following unique combination of characteristics which are outstanding therein and which distinguish our new variety from its parents, as well as from other varieties of which I am aware:

First: An extremely big plant, with florets of outstanding size, and a height of about seven feet.
Second: Peach colored florets.

In addition to these major characteristics my variety is also endowed with the following characteristics:

1. Consistently straight spikes
2. Exhibition type spikes
3. Extremely long stem, yet freedom from crooking
4. Good health
5. Admirable and consistent growth habits
6. Excellent propagative powers.

I have asexually reproduced the new variety by natural increase from cormels through several generations in New York, and succeeding generations have established that the distinguishing characteristics of the variety held true through propagations by plantings derived from cormels.

The accompanying drawing shows a typical specimen of a flower spike of the new variety, with the flowers in varied stages of growth. Some are shown as partially opened buds and others as fully opened buds. The flower is somewhat more peach colored than was possible to achieve in this type of reproduction.

The following is a detailed description of my new variety, with color terminology in accordance with the Horticultural Colour Charts issued by the British Colour Council and the Royal Horticultural Society, except where general color terms of ordinary dictionary significance are obvious.

PLANT

Growth: Vigorous, healthy, excellent propagator attaining a height of 72 to 88 inches.
Blooming Habit: Comes into bloom, under normal conditions, in approximately 90 days, in northeastern latitudes of the United States, after planting.
Stems:
*Form.*—Exceptionally straight.
*Diameter at base.*—About one inch.
*Color at base.*—Creamy white base of stem just above bulb.
Foliage: Above the ground leaves are bright green. The leaves of this variety are of slightly brighter green than most varieties. The average leaf is two and one-fourth inches wide at the base, and the foliage excluding the flower spike is forty to forty-two inches high, drooping artistically from the spot where the taper begins. Stem of flowerhead also has bright green cast.
Disease Resistance: The variety has been found to be unusually resistant to the usual gladiolus plant diseases of a bacterial, viral or fungoid genesis.
Corms: Mature corms are round and high crowned with smooth husks which have light brown cast.
*Color of flesh.*—Cream.

FLOWER

Spike:
*Form and size.*—Straight and very tall with flowerhead of 42 to 46 inches and regularly carrying 28 to 30 buds.
Bud:
*Size.*—About 3½ inches long when opening.
*Opening.*—On first blooming 3 or 4 buds open with 8 to 10 opening at one time thereafter.
Flower:
*Arrangement.*—Flowerhead of the new variety has an informal placement.
*Size.*—Individual florets are extremely large, averaging about 6½ to 7 inches in diameter.
*Form.*—Florets have triangularly arranged outside petals and offset triangularly arranged inside petals, the petals being only slightly ruffled.
*Keeping qualities.*—The flowers are long lasting.
Petals:
*Shape.*—Triangularly shaped with rounded sides.
*Size.*—Large upper petals, being about 3½ inches wide. Lip petals also large, being about 2½ inches wide.
*Aspect.*—Florets face up slightly, even when fully open. Petals are lightly ruffled at edges.
*Fragrance.*—None.
*Color.*—Peach colored at petal edegs fading into darker shades at edges and base of petals. Shrimp red—Plate 616 with outer edges 616/2 and shading 616/3 in throat.

REPRODUCTIVE ORGANS

Stamens:
*Color.*—Light rose.
Pistils:
*Color.*—Greenish white coming out of calyx and where stamens and pistil develop.

GROWTH

Locality where grown and observed: Long Island, N.Y.
Propagation: Holds its distinguishing characteristics through succeeding propagations from cormels.

It can be seen that this variety is unique in its large size, being tall with large florets, and in its peach (shrimp red) color.

What I claim is:

1. A new and distinct variety of gladiolus plant, substantially as herein shown and described, characterized particularly as to novelty by the unique combination of its extremely large size and its peach color.

No references cited.

ROBERT E. BAGWILL, Primary Examiner